United States Patent [19]

Howes

[11] Patent Number: 4,894,057
[45] Date of Patent: Jan. 16, 1990

[54] FLOW ENHANCED MULTI-LUMEN VENOUS CATHETER DEVICE

[76] Inventor: Randolph M. Howes, 4540 Fort Macomb Rd., New Orleans, La. 70129

[21] Appl. No.: 63,918

[22] Filed: Jun. 19, 1987

[51] Int. Cl.⁴ ............................................. A61M 25/00
[52] U.S. Cl. ..................................... 604/280; 604/43; 604/53; 604/83
[58] Field of Search ....................................... 604/45–45, 604/52, 53, 280–283, 82–83, 56; 128/207.15

[56] References Cited

U.S. PATENT DOCUMENTS

| | | | |
|---|---|---|---|
| Re. 31,873 | 4/1985 | Howes | 128/675 |
| 550,238 | 11/1895 | Allen | 604/101 |
| 1,696,018 | 12/1928 | Schellberg | 604/43 |
| 2,286,462 | 6/1942 | Chaffin | 604/43 |
| 2,845,930 | 8/1958 | Brown | 604/97 |
| 2,954,982 | 10/1958 | Pagano | 604/101 |
| 3,046,988 | 7/1962 | Moreau et al. | 128/325 |
| 3,055,361 | 9/1962 | Ballard | 604/163 |
| 3,144,868 | 8/1964 | Jascalevich | 604/43 |
| 3,359,974 | 12/1967 | Khalil | 128/713 |
| 3,370,587 | 2/1968 | Vizcarra | 604/53 |
| 3,435,819 | 4/1969 | Reynolds et al. | 128/675 |
| 3,437,088 | 4/1969 | Bielinski | 128/748 |
| 3,566,874 | 3/1971 | Sheperd et al. | 604/265 |
| 3,583,404 | 6/1971 | McWhorter | 604/99 |
| 3,626,471 | 12/1971 | Florin | 128/20 |
| 3,640,269 | 2/1972 | Delgado | 604/43 |

(List continued on next page.)

FOREIGN PATENT DOCUMENTS

| | | | |
|---|---|---|---|
| 960932 | 1/1975 | Canada | |
| 2513520 | 4/1983 | France | 604/280 |

OTHER PUBLICATIONS

Buckel, et al., The Journal of Physiology, vol. 242 No. 2 Oct. 24, 1974, Cambridge University Press, pp. 55, 56.
Christopher W. Hauge, et al., Annals of Surgery, vol. 162, No. 6 Dec., 1965, L. B. Lippincott Company, pp. 1028–1038.
Cournand et al. "Double Lumen Catheter for Intravenous and Intracardic Blood Sampling and Pressure Recording" Proc. Soc. Exp. Biol. Med. Co. 60: 73–75 (1945).
Bierman "Selective Arterial Catheterization." Charles C. Thomas, Publisher (1969).
"Cardiology Radiology Surgery" USCI 1967–1968.
"Cardiovascular Catheters and Accessories" USCI 1974.
"Edwards Laboratories, Swan–Ganz Flow–Directed Monitoring Catheters," 1974.
"The Swan–Ganz Flow–Directed Thermodiultion Catheter," 1974.

Primary Examiner—Dalton L. Truluck
Attorney, Agent, or Firm—Finnegan, Henderson, Farabow, Garrett & Dunner

[57] ABSTRACT

A venous catheter device includes an elongated flexible catheter tube having a proximal end and a longitudinally extending the distal end portion with a catheter tube distal terminus for insertion into and capable of being fed longitudinally through a vein. A plurality of independent lumens extend through the catheter tube, preferably including a distal lumen, a middle lumen and a proximal lumen, each of the lumens having a wall, a proximal end, and a lumen distal terminus adjacent to the catheter tube distal terminus. Each lumen distal terminus spaced longitudinally from each other so as to include a distal lumen terminus, a middle lumen terminus, and a proximal lumen terminus, respectively. At least two of the lumen termini have a fluid flow enhancement structure for maximizing fluid flux rate through each lumen by directing flow through the distal terminus of each lumen in a direction parallel to the longitudinal direction of the distal end portion. Each of the proximal ends of the lumens include lumen adaptors for connection to independent fluid devices. It is preferable that the fluid flow enhancement structure includes longitudinal grooves located in the outer wall of the distal end portion and axially aligned with the respective lumens.

11 Claims, 3 Drawing Sheets

U.S. PATENT DOCUMENTS

| | | | |
|---|---|---|---|
| 3,695,921 | 10/1972 | Sheperd et al. | 604/265 |
| 3,710,781 | 1/1973 | Huthcins | 128/2.05 D |
| 3,726,281 | 4/1973 | Norton et al. | 604/96 |
| 3,788,326 | 1/1974 | Jacobs | 128/207.15 |
| 3,805,794 | 4/1974 | Schlesinger | 604/103 |
| 3,815,608 | 6/1974 | Spinosa et al. | 604/104 |
| 3,867,945 | 2/1975 | Long | 604/104 |
| 3,885,567 | 5/1975 | Ross | 604/43 |
| 3,963,028 | 6/1976 | Cooley et al. | 604/902 |
| 3,995,623 | 12/1976 | Blake et al. | 128/642 |
| 4,057,065 | 11/1977 | Thow | 604/101 |
| 4,100,246 | 7/1978 | Frisch | 264/230 |
| 4,106,509 | 8/1978 | McWhorter | 604/103 |
| 4,405,313 | 9/1983 | Sisley et al. | 604/43 |
| 4,406,656 | 9/1983 | Hattler et al. | 604/43 X |
| 4,543,087 | 9/1985 | Sommercorn et al. | 604/43 |
| 4,568,329 | 2/1986 | Mahurkar | 604/43 |
| 4,583,968 | 4/1986 | Mahurkar | 604/43 |
| 4,601,701 | 7/1986 | Mueller | 604/83 |
| 4,643,711 | 2/1987 | Bates | 604/43 X |

FLOW ENHANCED MULTI-LUMEN VENOUS CATHETER DEVICE

BACKGROUND OF THE INVENTION

The invention relates to venous catheter devices, and more particulary, to a single catheter device that may be used to infuse multiple fluids, including nourishment and drugs, crystalloids, colloids, and blood and/or blood products, simultaneously into a patient's vein. In addition, the catheter of the present invention may be used for central venous pressure (CVP) monitoring and/or removal of blood samples simultaneously with drug and/or fluid infusion. Even more particularly, the present invention relates to multi-lumen venous catheter devices such as those disclosed in U.S. Pat. No. Re. 31,873 to Randolph M. Howes, the disclosure of which is incorporated herein by reference.

The Howes '873 patent discloses a multi-lumen venous catheter device having a distal end portion generally circular in cross-section and having a uniform outer diameter. The distal termini of lumens are spaced from each other. One lumen has a distal terminus adjacent the distal terminus of the catheter tube. The distal termini of the other lumens provide exits at lateral openings in the distal end portion of the catheter tube.

Since the catheter device shown in the Howes '873 patent has multiple lumens which are adapted for multiple and simultaneous operations through use of a single catheter tube, it provides a substantial advance over conventional venous catheter devices by reducing the number of catheter devices required to be inserted in a patient at a single time when performing multiple functions or procedures. It also prevents the drugs and fluids from mixing prior to entering the bloodstream thereby avoiding incompatibility problems. In addition, it minimizes patient discomfort and decreases the possibility of associated complications such as infection and bleeding.

Even though undesirable mixing is prevented and patient discomfort is minimized by this arrangement of longitudinally spaced lumen termini in a multi-lumen catheter tube with a uniform outer diameter, the fluid flux rate through the lumens is reduced relative to the fluid flux rate of some single lumen catheters previously available.

The catheters shown in the Howes '873 patent also create turbulence and provide sites for blood material such as platelets and red blood cells to accumulate or be deposited and form clots due to thrombus and fibrinogen accumulation.

Accordingly, it is an object of the present invention to provide a multi-lumen venous catheter device having the advantages of the devices disclosed in the Howes '873 patent, which permits infusion of a plurality of fluids into a patient's vein simultaneously through a single catheter without mixing the fluids before entering the bloodstream, while improving the fluid flux rate through each lumen and minimizing sites for the accumulation of deposits of materials likely to initiate clot formation.

It is a further object of the present invention to provide a venous catheter device with multiple lumens which has these advantages and which also allows improved infusion flow rates of liquids into a vein.

It is an additional object to the present invention to provide a venous catheter device with multiple lumens which can be interchangeably used in a more efficient and reliable manner for the various purposes for which it is designed.

It is also an object of the present invention to provide a venous catheter device with multiple lumens which is more forgiving during infusion processes in the event an improper pressure differential, flow rate or drug concentration is used.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects and in accordance with the purposes of the invention as embodied and broadly described herein, there is provided a venous catheter device comprising: an elongated flexible catheter tube having an outer wall, a proximal end and a longitudinally extending distal end portion with a catheter tube distal terminus for insertion into and capable of being fed longitudinally through a vein; a plurality of independent lumens extending through the catheter tube, each lumen having a lumen distal terminus in the distal end portion, the lumen distal terminus of at least one of the lumens being spaced longitudinally from the lumen distal terminus of at least one other of said lumens, at least one lumen distal terminus communicating with fluid flow enhancement means provided in the outer wall of said catheter tube; and lumen adapter means provided at the proximal ends of said lumens for permitting connection of said lumens to independent devices.

It is preferable that at least three independent lumens extend through the catheter tube including a distal lumen, a middle lumen and a proximal lumen; each of the lumens having a wall, a proximal end and a lumen distal terminus adjacent the catheter tube distal terminus; each lumen distal terminus being spaced longitudinally from each other so as to include a distal lumen distal terminus, a middle lumen distal terminus, and a proximal lumen distal terminus, respectively; at least two of the lumen distal termini having fluid flow enhancement means for directing flow through the lumen distal terminus in a direction substantially parallel to the longitudinal direction of the distal end portion. It is further preferable that the fluid flow enhancement means include a longitudinal groove located in the outer wall of the distal end portion, axially aligned and continuous with a respective lumen.

The catheter of the present invention differs from the design of the catheter described in Howes U.S. Pat No. Re. 31,873 in that instead of having a distal end portion which is generally circular in cross-section and of uniform outer diameter, the present catheter, in its preferred form, has a distal end portion which is of irregular and diminishing cross-section in the area where the lumens terminate.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DESCRIPTION OF THE PREFERRED EMBODIMENT

Reference will now be made in detail to the present preferred embodiment of the invention as illustrated in the accompanying drawings.

In accordance with the present invention, the venous catheter device includes an elongated flexible catheter tube having an outer wall, a proximal end and a longitudinally extending distal end portion with a catheter tube distal terminus for insertion into and capable of being fed longitudinally through a vein.

Figure 1:
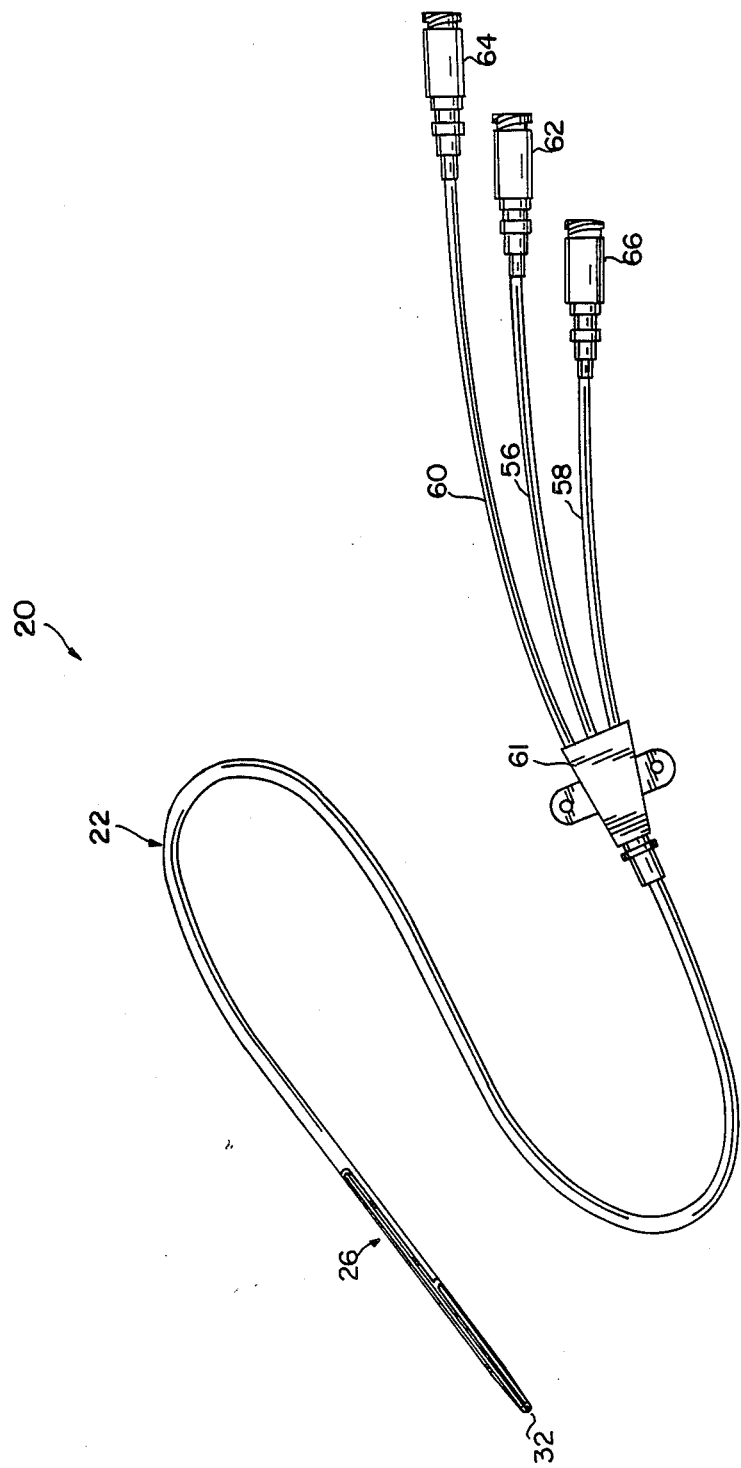
FIG. 1 shows a catheter device constructed in accordance with a preferred form of the invention.
Figure 7:
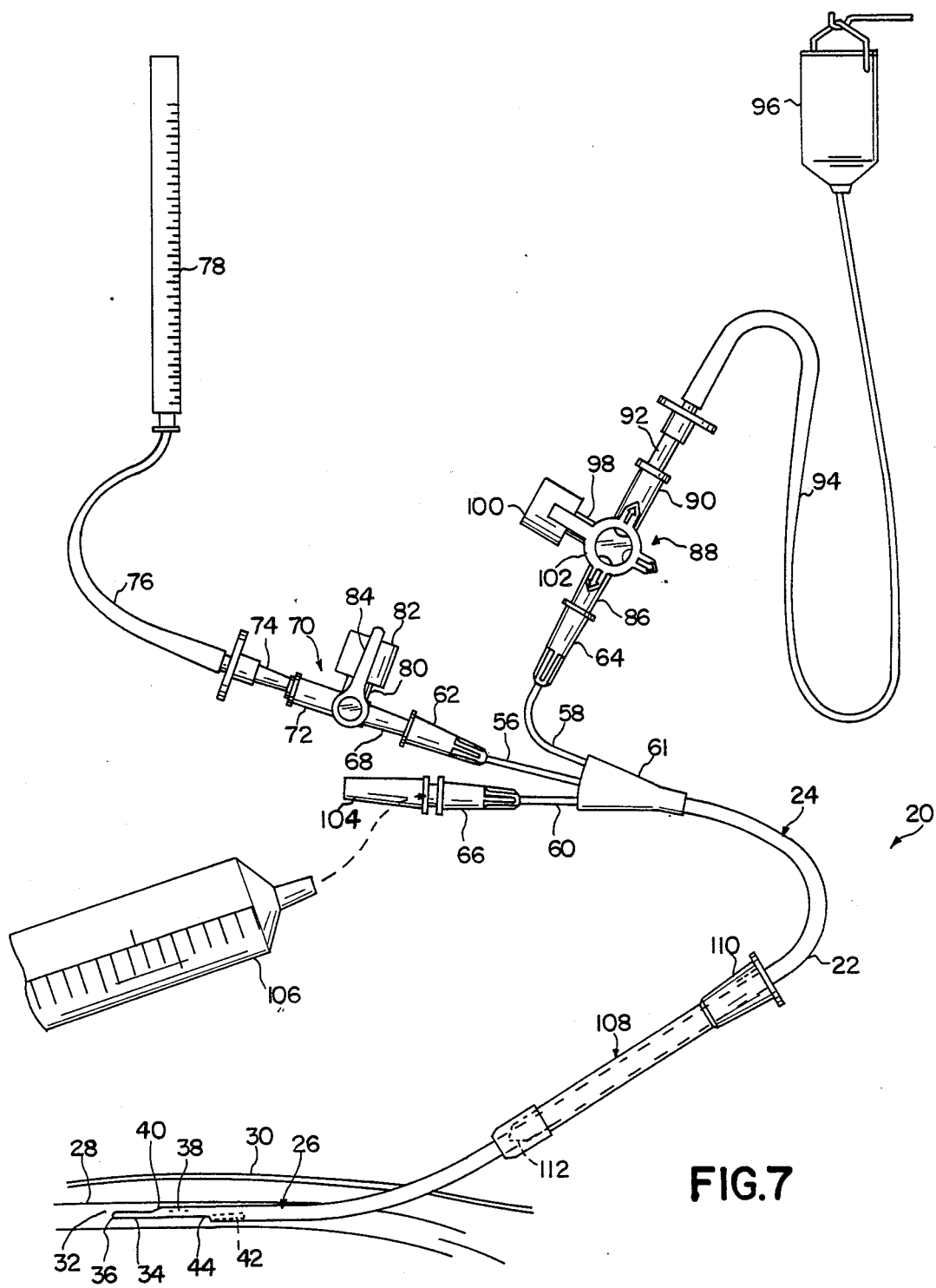
FIG. 7 is a side elevation view of the catheter shown in FIG. 1, positioned in a vein, with a venipuncture needle withdrawn and protected, and with the catheter connected to a variety of fluid devices.

As shown in FIGS. 1 and 7, the venous catheter device includes catheter 20. The elongated flexible catheter tube includes elongated flexible tube 22. The proximal end of the catheter tube 22 includes proximal end 24 which is connected to fluid or other devices.

The longitudinally extending distal end portion of catheter tube 22 comprises the distal end portion 26 of catheter tube 22 which is inserted into a vein 28 beneath the skin 30 of a patient. As shown in FIG. 7, blood flows through vein 28 in a leftward direction as shown by the arrow. In addition, distal end portion 26 of catheter tube 22 is inserted into and is fed longitudinally through vein 28 in the leftward direction as shown. The distal end portion 26 has a distal terminus 32.

In accordance with the present invention there is provided a plurality of independent lumens extending through the catheter tube, each lumen having a lumen distal terminus in the distal end portion of the catheter. The lumen distal terminus of at least one of the lumens is spaced longitudinally from the lumen distal terminus of at least one other of said lumens. It is preferable that the plurality of lumens include at least three independent lumens extending through the catheter tube, including a distal lumen, a middle lumen and a proximal lumen. Each of the lumens has an inner wall, a proximal end and a lumen distal terminus adjacent to the catheter tube distal terminus. The lumen distal termini are spaced longitudinally from each other so as to include a distal lumen distal terminus, a middle lumen distal terminus, and a proximal lumen distal terminus, respectively.

As used herein, "lumen" is intended to mean fluid conduit means and may include individual tubes, or elongated openings or passages formed in a body, or it may include individual tubes connected to elongated passages in a body. "Independent lumens" is intended to mean lumens which do not communicate flow between each other.

Figure 2:
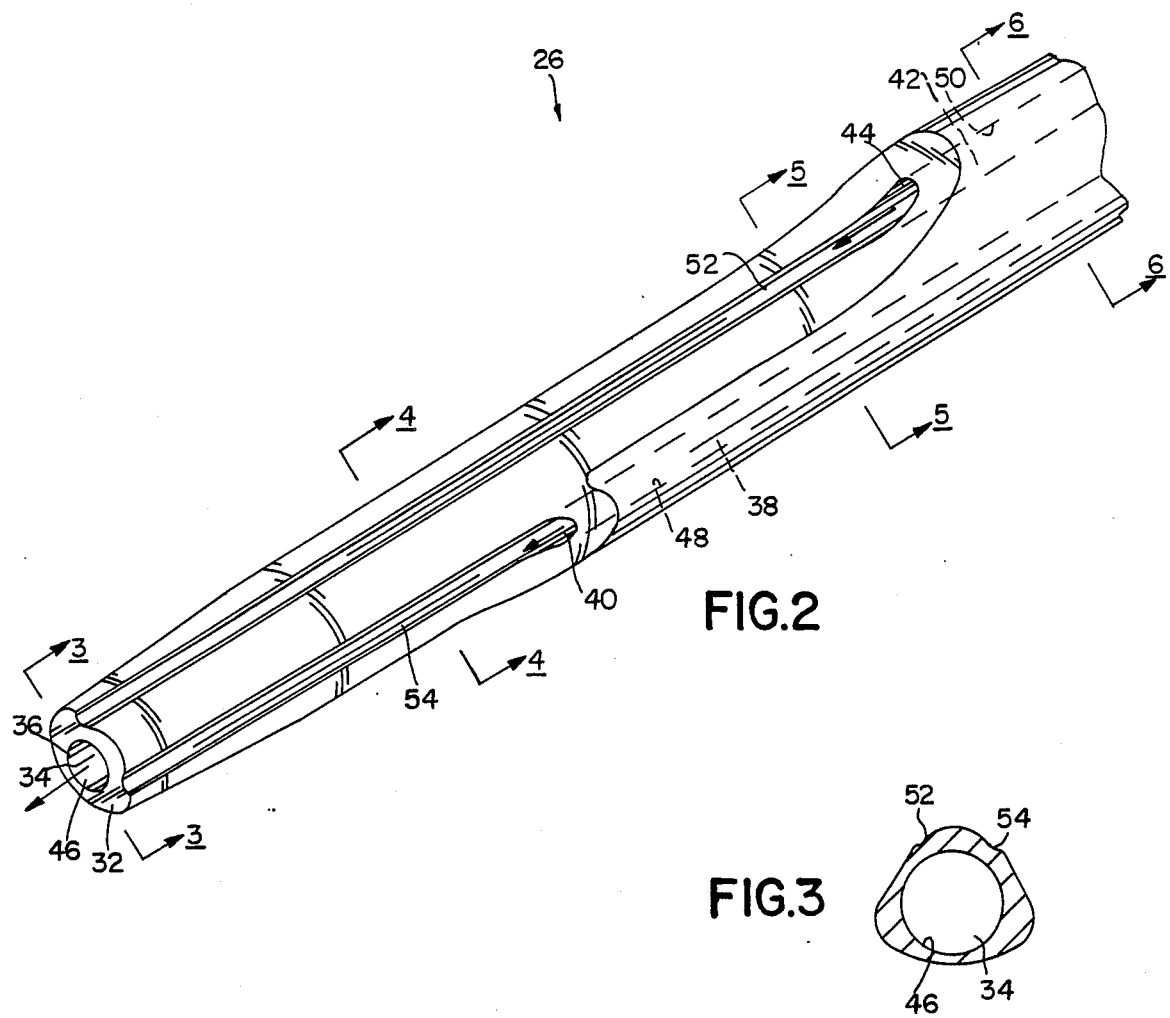
FIG. 2 is an enlarged partial perspective view of the distal tip of the catheter device shown in FIG. 1.
Figure 3:
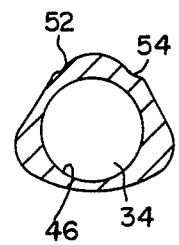
FIG. 3 is a cross-section view of the catheter device taken along line 3—3 of FIG. 2.
Figure 4:
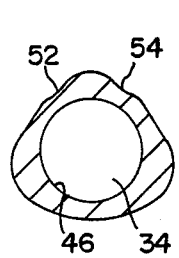
FIG. 4 is a cross-section view of the catheter device taken along line 4—4 of FIG. 2.
Figure 6:
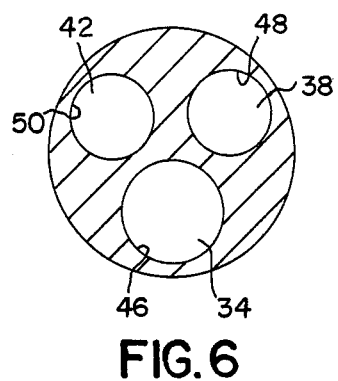
FIG. 6 is a cross-section view of the catheter device taken along line 6—6 of FIG. 2.

As shown in FIGS. 2 and 6, the distal, middle and proximal lumens are so named to indicate the relative positions of their respective termini on catheter tube distal end portion 26. Distal lumen 34 extends from the catheter tube proximal end 24 through the catheter tube to distal end portion 26 where it terminates at the lumen distal terminus 36. Middle lumen 38 extends from the catheter tube proximal end 24 through the catheter tube to middle lumen distal terminus 40. Proximal lumen 42 extends from catheter tube proximal and 24 through the catheter tube to proximal lumen distal terminus 44.

As shown in FIGS. 2 and 6, distal lumen 34 has a wall 46, middle lumen 38 has a wall 48, and proximal lumen 42 has a wall 50. Each of the lumen walls 46, 48 and 50, extends longitudinally through catheter tube 22 to form a slender passageway which extends to the respective lumen termini 36, 40 and 44 (also seen in FIG. 7).

The lumen termini (exit ports) 36, 40 and 44 are longitudinally spaced from each other by at least about one centimeter and up to about three centimeters or more. Thus, when the catheter is positioned in a vein, two or more fluids, or agents such as dyes or medicines, can be infused simultaneously into the bloodstream using any of the lumens 34, 38 and 42 without mixing prior to entry into the blood stream. A spacing of at least about one centimeter between lumen termini is generally sufficient to prevent any mixing problem.

According to the present invention, at least one lumen distal terminus communicates with unique fluid flow enhancement means provided in the outer wall of the catheter tube. It is preferable that each of the middle and proximal lumen termini have a fluid flow enhancement means for maximizing fluid flux rate through each lumen by directing flow through the distal terminus in a direction substantially parallel to the longitudinal direction of the distal end portion. It also is preferable that the fluid flow enhancement means include a longitudinal groove located in the outer wall of the distal end portion and axially aligned with a respective lumen. It is further preferable that the groove be an extension of the lumen which runs from the lumen distal terminus to the distal tip of the catheter. It is, however, not necessary that the groove extend all the way to the catheter tip.

As shown in FIG. 2, the fluid flow enhancement means cooperating with proximal lumen terminus 44 includes longitudinally extending groove 52 which is located in the outer wall of distal end portion 26 and is axially aligned with and a continuation of proximal lumen 42. Longitudinal flow through proximal lumen 42 continues in an uninterrupted fashion in the longitudinal direction through proximal lumen terminus 44 and into groove 52, where mixing with the blood stream occurs.

Similarly, the fluid flow enhancement means cooperating with middle lumen terminus 40 includes longitudinally extending groove 54 which is located in the outer wall of distal end portion 26 and is axially aligned with and continuous from middle lumen 38. Longitudinal flow through middle lumen 38 continues in an uninterrupted fashion in the longitudinal direction through middle lumen terminus 40 and into groove 54, where mixing with the blood stream occurs.

The catheter disclosed in Howes U.S. Pat. No. Re. 31,873 incorporates lumen exit ports which are spaced from the distal terminus of the catheter tube and which constitute lateral openings in the tube. The distal end portion of the '873 catheter is generally circular in cross-section and has a uniform outer diameter. In contrast, provision of fluid flow enhancement means in the catheter of the present invention enables infused fluids to flow through all the lumen distal termini in a direction parallel to the longitudinal direction of the distal end portion. This improved flow pattern is permitted by the irregular and diminishing cross-section of the distal end portion from the point of the proximal lumen terminus to the tip. As a result, the present invention infuses fluids in a different and more efficient manner and with less turbulence at the exit site of the lumen distal termini than the venous catheter device disclosed in the Howes '873 patent.

The improved flow characteristics and reduced turbulence minimize the number of blood or blood component accumulation sites and reduce the risk of clotting. In the Howes '873 catheter, the flow through the lumen opening has a substantial component in the lateral direction and a minimum component, if any, in the axial direction because there is a buttress adjacent to the laterally-directed lumen exit ports. In the present device there is a substantial component of axial flow through the lumen openings because of the unique shape of the catheter wall adjacent to the middle and proximal lumen exit ports 40 and 44.

The proximal ends of the lumens are connected to adaptor means for coupling the lumens to independent fluid and/or other devices. As shown in FIG. 7, a Y connector 61 couples the lumens 34, 38 and 42 with tubes 56, 58 and 60, respectively. Tubes 56, 58 and 60 are provided with adaptors 62, 64, 66, respectively, for attachment to suitable fluid and/or other devices. The adaptor 62 is shown as connected to one leg 68 of a flow control valve 70 which may, in turn, have another leg 72 receiving a fitting 74 fixed to one end of a conduit 76 for a central venous pressure (CVP) measuring device 78. Still another leg 80 of valve 70 may be connected to another fluid source and/or other device (not shown) which may be alternatively communicated with leg 68 and tube 56. As shown, leg 80 is closed off by a cap 82. A control lever 84 of valve 70 is turnable to open and close communication between the valve legs 72, 80, and valve leg 68. In the position shown, valve legs 68 and 72 are connected and CVP device 78 is operative with other alternatives readily available.

Adaptor 64 is shown connected to one leg 86 of stop cock valve 88. Another leg 90 of valve 88 receives a fitting 92 fixed to conduit 94 connected to an IV bottle or bag 96. A third leg 98 of valve 88 is shown closed off by a cap 100. A control knob 102 on valve 88 selectively couples leg 86 with leg 90 or leg 98. In the position shown, legs 86 and 90 are connected so that fluid from the IV bottle or bag is flowing into tube 58.

Finally, adaptor 66 has a flow plug 104 fitted therein to seal off tube 60. However, this plug can be removed and adaptor 66 fitted with a syringe 106 for infusing drugs or taking blood samples as can adaptor 64.

If desired, adaptors 62, 64 and 66 may each be coupled to a fluid source such as IV bottle or bag 96 so that three fluids may be infused intravenously at the same time at maximal or differing rates of flow.

Lumens 34, 38 and 42 are independent of and noncommunicative with one another so that fluids carried by the lumens will not mix prior to entering into the bloodstream. In addition, as described, lumens 34, 38 and 42 can be used simultaneously for CPU monitoring, fluid infusion, injection, and/or blood sampling. This independence of lumens allows a patient's CVP to be monitored, and, if desired, blood samples to be taken, at the same time fluids are being administered, and all of this is achieved with one vein puncture if a hollow needle or insertion device is used, or one vein exposure and partially transectioned if a hollow needle or insertion device is not used. As shown in FIG. 7, a hollow needle 108, supported at one end by hollow needle hub 110 can be used. The other end of hollow needle 108 is formed with a sharpened and tapered tip 112 for penetrating the skin 30 and a vein 28 of a patient.

The present invention is different from the arrangement shown in the Howes '873 patent because the various lumens of the present invention can be interchangeably used in a more reliable manner for the various purposes for which it is designed. For example, the arrangement shown in the Howes '873 patent is disclosed as being able to best monitor CVP measurement by using the lumen which exits centrally of the catheter tube at the distal tip since that lumen does not contact the vein wall which otherwise might distort pressure readings obtained. With the arrangement of the present invention, the fluid flow enhancement means reduces the interaction of the vein wall at the lumen distal terminus of both the proximal and middle lumens. This allows more accurate CVP measurement at any of the lumens.

The longitudinal flow direction provided by the flow enhancement means of the present invention also helps prevent damage to the vein wall during infusion processes if an improper pressure differential, flow rate or drug concentration is used.

Figure 5:
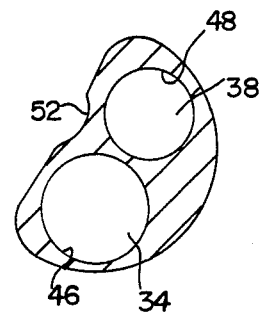
FIG. 5 is a cross-section view of the catheter device taken along line 5—5 of FIG. 2.

As shown in FIGS. 2 through 6, the section of the distal end portion 26 which is below lumen distal terminus 44 has a cross-section of substantially reduced diameter relative to the diameter of tube 22 as seen in FIG. 6. The reduced cross-section as shown in FIG. 5 reduces further to that shown in FIG. 4, and then to that shown in FIG. 3, as the tip of the catheter is approached.

This progressive step-wise pattern of substantially reducing the diameter of the distal end portion 26 and the fluted distal end shape of the present invention differs with respect to the catheter device of the Howes '873 patent where the distal end portion is generally circular in cross-section and has a uniform outer diameter.

It is preferable, although not essential, that the grooves of the fluid flow enhancement means adjacent to the proximal lumen terminus and the middle lumen terminus extend to the catheter tube distal terminus. As shown in FIG. 2, grooves 52 and 54 extend from proximal lumen terminus 44 and middle lumen terminus 40 to the distal terminus 32 of the catheter tube.

The elongated flexible catheter tube may be formed by processes such as molding or extruding a molten plastic or other synthetic material into the disclosed structure. The lumens may be formed by molding or extruding the catheter tube in one piece as an integral unit or by forming the lumens by using individual tubes, separate from the flexible catheter tube and assembling the lumens in the catheter tube.

The lumen distal termini may be formed by removing a section of the distal end portion of the catheter tube which longitudinally extends substantially from the catheter tube distal terminus to an area longitudinally spaced from the catheter tube distal terminus. This removal step may be accomplished by using a heated die or mold or by cutting away a section of the wall of the catheter tube to expose the wall of a longitudinally freely extending lumen.

The multi-lumen catheter device of the present invention can be seen to have the advantages present in the venous catheter device disclosed in the Howes '873 patent. However, it can also been seen that it is structurally and functionally different and distinguished from the device shown in the Howes '873 patent so that it provides significant and substantial benefits in comparison to the device shown in the Howes '873 patent.

Additional advantages and modifications will readily occur to those skilled in the art. The invention in its broader aspects is, therefore, not limited to the specific details, representative apparatus and illustrative example shown and described. Accordingly, departures may be made from such details without departing from the spirit or scope of the general inventive concept as defined by the appended claims and their equivalents.

What is claimed is:

1. A venous catheter device comprising:
   an elongated flexible catheter tube having an outer wall, a proximal end and a longitudinally extending distal end portion with a catheter tube distal terminus for insertion into and capable of being fed longitudinally through a vein;
   at least three independent lumens extending through said catheter tube including a distal lumen, a middle lumen and a proximal lumen;
   each of said lumens having a wall, a proximal end and a lumen distal terminus formed in said longitudinally extending distal end portion;
   said lumen distal termini being spaced longitudinally from each other to define a diatal lumen distal terminus, a middle lumen distal terminus, and a proximal lumen distal terminus, respectively;
   at least two of said distal lumen termini cooperating with groove means located in the outer wall of said distal end portion and communicating with said at least two distal lumen termini for providing a flow-enhanced outflow path from said at least two distal lumen termini along the outer wall of said distal end portion, and each of the proximal ends of said lumens including lumen adapter means for permitting connection to independent fluid devices.

2. The venous catheter device of claim 1 wherein said groove extends to the catheter tube distal terminus.

3. The venous catheter device of claim 1 wherein the outer wall of the distal end portion adjacent the groove has a substantially reduced diameter relative to the diameter of the outer wall of the distal end portion proximal of the distal terminus of said respective lumen.

4. The venous catheter device of claim 1 wherein the distal terminus of one of said lumens is substantially coextensive with the distal terminus of said catheter tube.

5. The venous catheter device of claim 1 wherein said groove means comprises at least two grooves, one of said grooves being continuous with a portion of the wall of said proximal lumen.

6. The venous catheter device of claim 1 wherein said groove means comprises at least two grooves, one of said grooves being continuous with a portion of the wall of said middle lumen.

7. The venous catheter device of claim 1 wherein a first lumen terminus is spaced about one to three centimeters from the catheter tube distal terminus and a second lumen terminus is spaced about one to three centimeters from said first lumen terminus.

8. A method of constructing a venous catheter device comprising:
   forming an elongated flexible catheter tube having an outer wall, a proximal end, a longitudinally extending distal end portion, and a distal terminus;
   forming at least three independent lumens extending through the catheter tube including a distal lumen with a distal lumen terminus, a middle lumen and a proximal lumen, each having a proximal end; and
   forming a middle lumen distal terminus longitudinally spaced from the distal lumen terminus in the distal end portion of the catheter tube;
   forming a proximal lumen distal terminus in the distal end portion of the catheter tube longitudinally spaced from the middle lumen distal terminus;
   forming groove means in the outer wall of the distal end portion to communicate with said middle and proximal lumens for providing a flow-enhanced outflow path from the middle and proximal lumens along the longitudinal direction of the distal end portion of the catheter.

9. The method of claim 8 wherein the step of forming the middle lumen distal terminus includes removing a section of the distal end portion of the catheter tube which longitudinally extends substantially from the catheter tube distal terminus to an area longitudinally spaced from the catheter tube distal terminus.

10. The method of claim 8 wherein the step of forming the proximal lumen distal terminus includes removing a section of the distal end portion of the catheter tube which longitudinally extends substantially from the catheter tube distal terminus to an area longitudinally spaced from the catheter tube distal terminus and the middle lumen distal terminus.

11. The method of claim 8 including the step of providing the proximal end of the lumens with lumen adapter means for connection to independent fluid devices.

* * * * *